(12) United States Patent
Balducci

(10) Patent No.: US 8,792,094 B2
(45) Date of Patent: Jul. 29, 2014

(54) APPARATUS, SYSTEM AND METHOD FOR DETECTING DEFECTS OF METALLIC LIDS

(75) Inventor: Massimo Balducci, Imola (IT)

(73) Assignee: SACMI Cooperativa Meccanici Imola-Societa' Cooperativa (IT)

(*) Notice: Subject to any disclaimer, the term of this patent is extended or adjusted under 35 U.S.C. 154(b) by 224 days.

(21) Appl. No.: 13/508,038

(22) PCT Filed: Oct. 25, 2010

(86) PCT No.: PCT/IT2010/000427
§ 371 (c)(1),
(2), (4) Date: Jul. 6, 2012

(87) PCT Pub. No.: WO2011/055397
PCT Pub. Date: May 12, 2011

(65) Prior Publication Data
US 2012/0268733 A1    Oct. 25, 2012

(30) Foreign Application Priority Data
Nov. 4, 2009   (IT) .............................. RM2009A0567

(51) Int. Cl.
*G01N 21/00*   (2006.01)
*G01N 21/88*   (2006.01)

(52) U.S. Cl.
CPC ................................. *G01N 21/8806* (2013.01)
USPC ..................................... 356/237.2; 356/237.3

(58) Field of Classification Search
None
See application file for complete search history.

(56) References Cited

U.S. PATENT DOCUMENTS

2004/0175027 A1   9/2004   Mahon et al.
2008/0212318 A1   9/2008   Wang

FOREIGN PATENT DOCUMENTS

| EP | 0729572 B1 | 9/1996 |
| EP | 1637868 A1 | 3/2006 |
| JP | 11 295047 A | 10/1999 |
| WO | 91/06846 A1 | 5/1991 |

OTHER PUBLICATIONS

PCT Search Report of International Application No. PCT/IT2010/000427 filed on Oct. 25, 2010 in the name of SACMI Cooperativa Meccanici Imola—Societa' Cooperativa. Mail Date: Mar. 3, 2011.
PCT Written Opinion of International Application No. PCT/IT2010/000427 filed on Oct. 25, 2010 in the name of SACMI Cooperativa Meccanici Imola—Societa' Cooperativa. Mail Date: Mar. 3, 2011.

*Primary Examiner* — Tarifur Chowdhury
*Assistant Examiner* — Amanda Merlino
(74) *Attorney, Agent, or Firm* — Steinfl & Bruno LLP

(57) ABSTRACT

An apparatus for detecting defects of elements to be subjected to examination, particularly metallic lids, with means for lighting an element to be subjected to examination, an image acquisition unit, and a unit for processing images acquired by said image acquisition unit is described.

15 Claims, 8 Drawing Sheets

APPARATUS, SYSTEM AND METHOD FOR DETECTING DEFECTS OF METALLIC LIDS

CROSS REFERENCE TO RELATED APPLICATIONS

This application is the U.S. national stage of International Application PCT/IT2010/000427 filed on Oct. 25, 2010, which in turn claims priority to Italian Patent Application No. RM2009A000567 filed Nov. 4, 2009, both of which are herein incorporated by reference in their entirety.

The present invention relates to an apparatus for detecting defects of elements to be subjected to examination, particularly metallic lids, system for detection of defects provided with said apparatus and relevant operation method.

More specifically, the invention relates to an apparatus for detecting lids, particularly metallic lids for tins, cans or other kind of metallic containers, mainly destined to containing food, said apparatus being particularly studied and realised for detecting surface defects such as scratches, contaminations, dings, re-entrance and like, in different portions of the lid.

The specification will be addressed in the following to detection of metallic lids for tins, but it is well evident that the same must not be considered limited to this specific use.

As it is well known, different kind of foodstuffs, such as legumes, vegetables, meat, ecc., are preserved within metallic containers or cans. Said cans are generally closed by substantially flat metallic lids, covered by a protection film. Said film is suitable to prevent contact between foodstuffs and lid metallic, so as to prevent that oxidation of metal can contact foodstuff contained within the container.

It must be taken into consideration that cans are usually subjected to remarkable mechanical stresses. Furthermore, it often occurs that foodstuffs are preserved for a very long time, often even for years.

It implies that said lids, placed on said tins, must have very strict constructive and qualitative characteristics, in order to prevent that possible mechanical defects, such as surface or edge dings, permit to air entering within the container, so as to destroy products contained therein, or that lid metal oxidations can contact the foodstuff.

Different system exist for checking metallic lids and like, able to discard defective lids, said systems comprising a conveyor belt, on which said lids to be subjected to examination are transported, a containment frame, preferably provided above said conveyor belt, that can take a not operative position and an operative position, on which a lid to be subjected to examination is placed, a light source, provided inside said containment frame, to lighten the lid. Said systems usually also comprise video means for detection of the lid under examination, connected with said light source and with said detection means, processing image so as to detect defects on said lid.

A recurrent problem well known to those skilled in the art is that of permitting detection of every kind of defects, and particularly surface scratches and curl dings.

An apparatus for inspection of lids according to known art is described in European Patent EP 0729572 B1, concerning a video detection system, provided with a LED array for generating a lighting along different wavelengths, with fixing means for said LED array, so that the latter can lighten a sample or element to be subjected to examination, and suitable power supply means, that can activate said LEDs on the basis of wavelengths, so as to generate a light or lightening from all, or only from part of LEDs, having such a wavelength selected between at least a first wavelength and a second wavelength. Said system is also provided with video-detection means, that can receive light diffused from the element to be subjected to examination.

Said video-detection means also comprise insulation means, substantially concerning filtering means, that can distinguish light received into a first wavelength and a second wavelength. Said filtering means are substantially of the optical type.

The system described improves reliability of known systems, since it permits lightening lid to be subjected to examination with different wavelengths, at different and consecutive time intervals, by said supply means, which are differentiated on the basis of the wavelength type. However, it has been noted that it has different problems when mainly detecting lid scratches and ribs. Furthermore, said system has productivity problems, since number of detections carried out by the system is equal to the number of wavelengths that can be emitted by lightening source and that supply means can select, thus reducing the control speed.

It is well evident that such a procedure is long, requiring too much time.

Further solutions for detecting different types of defects use a plurality of cameras. However, in such a case, a remarkable increase of processing time occurs, and in any case, on the basis of empirical analyses, it has been noted that it also this kind of solution is not reliable.

In view of the above, it is therefore object of the present invention that of providing an apparatus for checking lids that can detect different kind of defects at the same time, without the needing of activating different kind of lightening during different time intervals.

A further object of the present invention is that of suggesting an apparatus for checking lids, which is compact.

These and other results are obtained according to the invention by a detection apparatus that can emit radiation beams within a frequency range, so that each radiation beam emitted by suitable lightening means for lightening a lid to be subjected to examination realises an optical path making an incidence angle with respect to the surface of a lid to be subjected to examination which is directly or inversely proportional to the relevant emission frequency.

It is therefore specific object of the present invention, an apparatus for detecting defects of elements to be subjected to examination, particularly metallic lids, comprising means for lighting an element to be subjected to examination, an image acquisition unit for acquisition of images, such as a camera or like, able detecting image of said element to be subjected to examination lightened by said lighting means, a unit for processing images acquired by said image acquisition unit, suitable to detect said defects, characterized in that said lighting means emit radiation beams according two or more frequencies included within a range set beforehand, each one of said radiation beams lighting said element to be subjected to examination according to an optical path, individuating an incidence angle with respect to the surface of said element to be subjected to examination included between a grazing minimum incidence angle and a scattering maximum incidence angle, said lighting means being provided so that incidence angle realized by the optical path of each one of said radiation beams emitted by lighting means is directly proportional or inversely proportional with respect to the relevant emission frequency.

Always according to the invention, said grazing minimum incidence angle corresponds to the radiation beam emitted by said lighting means at lower frequency of said set range.

Still, according to the invention, said lighting means comprise a plurality of LED's for emission of said radiation beams, said LED's being provided so that incidence angle of radiation beam optical path emitted by each one of said LED's is directly proportional or indirectly proportional with respect to the emission frequency.

Furthermore, according to the invention, said lighting means comprise a diffuser, having a substantially hemispherical shape, with its concavity faced downward, provided at the top with a hole, through which said image acquisition unit detects image of said element to be subjected to examination, and in that said LED's of said first lighting means are grouped in a first, a second and a third LED assembly, said first LED assembly is installed according to a ring arrangement outside said diffuser, so as to grazing lighten said element to be subjected to examination, and it is suitable to emit at a first minimum frequency, preferably within the red field, said second LED assembly is installed according to a ring arrangement outside said diffuser, so as to lighten said element to be subjected to grazing scattering examination, and it suitable to emit at a second intermediate frequency, preferably within the green field, and said third LED assembly comprises a first LED assembly, installed according to a ring arrangement above said diffuser, and a second LED assembly, arranged vertically above said diffuser, so as to lighten said element to be subjected to scattering examination, and it is suitable to emit at a third intermediate frequency, preferably within the blue field.

Always according to the invention, said lighting means further comprise a beam splitter mirror, provided above said diffuser reflecting the radiation beam emitted by said second LED assembly on said element to be subjected to examination and permitting detection of image of said element to be subjected to examination by said image acquisition unit.

Still according to the invention, said apparatus comprises a protection hood, open at the bottom, within which said image acquisition unit and said lighting means are provided, the latter placed under said image acquisition unit.

Advantageously, according to the invention, said image processing unit can make an image digital filtering according to each one of said two or more frequencies, so as to automatically recognize said defects of each filtered image.

It is further object of the present invention a system for detection of defects on element o be subjected to examination, particularly metallic lids, comprising a conveyor belt, on which said elements to be subjected to examination are conveyed, an upright, substantially vertical with respect to said conveyor belt, a slide sliding coupled with said upright, and an apparatus for detecting defects of said elements to be subjected to examination, fixed to said slide, so that said apparatus can have a rest position, raised with respect to said conveyor belt, and an operative position, in a lowered mode to be above said element to be subjected to examination, so as to lighten the same and acquiring the image, characterized in that said apparatus for detecting defects is apparatus as defined in the above.

It is still object of the present invention a method for detecting defects of elements to be subjected to examination, particularly metallic lids, comprising the following steps:
  (a) lighting said element to be subjected to examination;
  (b) acquiring images of said element to be subjected to examination;
  (c) processing images of said element to be subjected to examination acquired during said step (b);
  characterized in that said element to be subjected to examination is lightened during said step (a) by radiation beams according two or more frequencies included within an interval set beforehand, each one of said radiation beams lightening said element to be subjected to examination according to an optical path individuating an incidence angle with respect to the surface of said element to be subjected to examination included between a grazing minimum incidence angle and a scattering maximum incidence angle, incidence angle made up of optical path of each one of said emitted radiation beams being directly o indirectly proportional to the relevant emission frequency.

Always according to the invention, said radiation beam emitted during said step (a) at the lower frequency of said set range corresponds to said incidence angle.

The present invention will be now described for illustrative but not limitative purposes according to its preferred embodiments, with reference to the figures of the enclosed drawings, wherein.

Same references will be used in the different views to indicate the same or similar parts.

Figure 1:
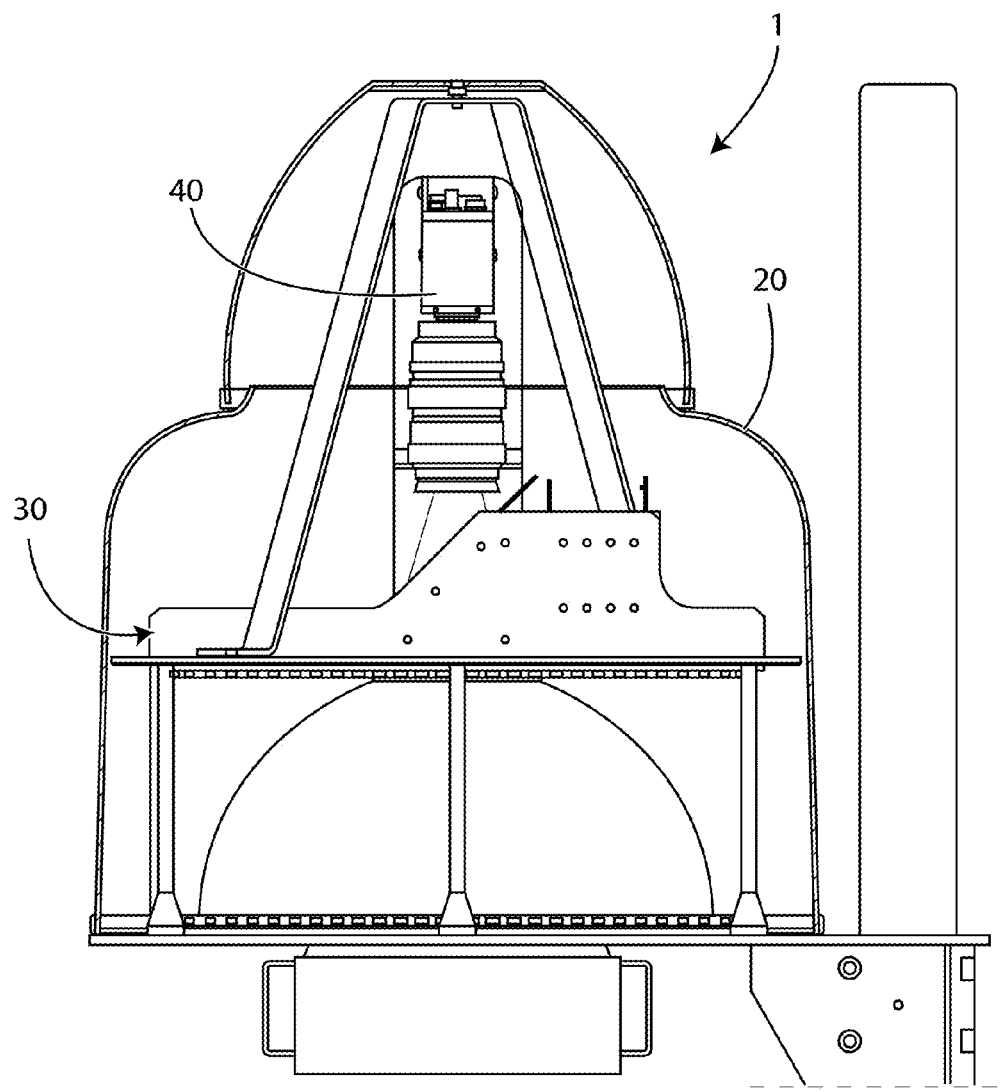
FIG. 1 shows an apparatus for detecting defects on elements to be subjected to examination, particularly on lids, according to the present invention.
Figure 2:
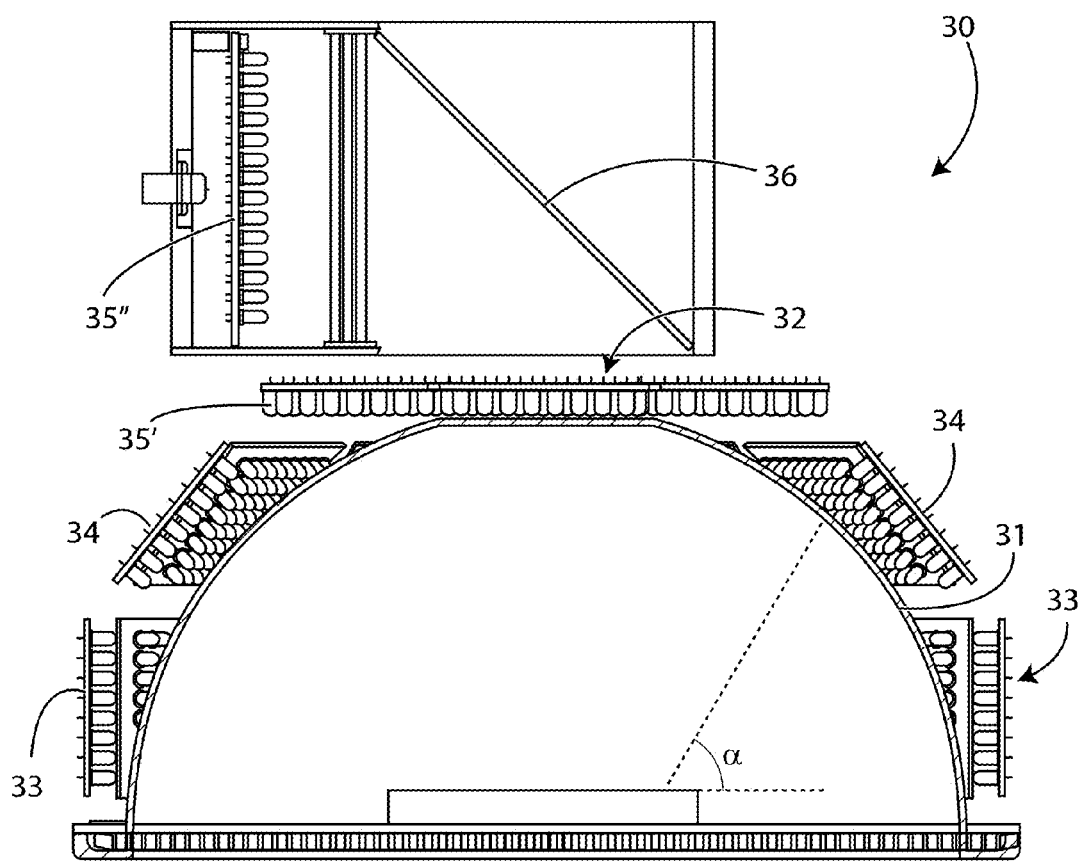
FIG. 2 shows a cross-section view of apparatus of FIG. 1.

Making reference to FIGS. 1 and 2, it is observed an apparatus 1 for detection of defects of metallic lids according to the present invention. Particularly, said apparatus 1 comprises a protection hood 20, open at the bottom, within which lighting means 30 for lighting the element to be subjected to examination are provided. Said apparatus 1 also comprises a colour camera 40, always provided within said protection hood 20, above said lighting means. Said colour camera 40 is placed so as to take image of surface of element or lid to be subjected to examination, which is lightened by said lighting means 30.

Said lighting means 30 and said camera 40 are connected to a suitable processing and controlling unit (not shown in the figures), comprising a processor which, besides coordinating lighting and image acquisition operations, also processes images acquired for detection of possible defects on said lids or elements to be subjected to examination.

FIG. 2 particularly shows an embodiment of said lighting means 30, comprising a diffuser 31, having a substantially hemi-spherical shape, provided with a hole 32 at the top. Said diffuser 31 is transparent and preferably comprised of PLEXIGLAS®. Function of said diffuser 31 will be better described in the following.

Said lighting means 30 also comprise a plurality of LEDs (Light Emitting Diode), grouped in three different groups, each one able to emit a radiation beam at a relevant frequency. Particularly, in this embodiment, they are provided a minimum frequency $f_1$ within the red domain for group 33, an intermediate frequency $f_2$ within the green domain for group 34, and a maximum frequency $f_3$ within the blue domain for group 35. Each one of said groups 33, 34 and 35 is provided in a specific position in order to prevent interference between beams emitted, as it will be better described in the following.

Particularly, a first group of LEDs 33, arranged according to a ring or circular arrangement, outside said diffuser 31, can grazing lighten the lid to be subjected to examination, i.e. according to a minimum a angle, said a angle being the angle individuated by grazing incident beam or ray with respect to horizontal plane surface of said lid to be subjected to examination. Said first LED group 33 emits at the minimum frequency within the red domain, and said radiation beam, should meet a defect (e.g. a scratch or ding) is scattered by the same. This causes a clear or dark detection of said defect by camera 40, permitting detecting also small scratches on plane surfaces of lids or small defects on curl.

A second group of LEDs 34, arranged according to a ring or circular arrangement, outside said diffuser 31, can grazing diffusion lighten said lid, with incidence angles α bigger than incidence angles of said first LED group 33. Said second LED group 34 is set to emit at said second frequency $f_2$ among the three frequencies provided, i.e. the one within the green domain. Said radiation beam, according to lid surface met (rib, curl, plane portion), is reflected or diffused. Said second LED group 34 is particularly suitable for detecting defects, such as dings, on ribs of the object under examination.

Finally, third group of LEDs 35 comprises a first LED group 35', arranged according to a ring or circular arrangement, in correspondence of the top of said diffuser 31, and a second LED group 35", placed vertically above the diffuser 31. Radiation beam emitted by said second LED group 35" is directed on lid under examination by a beam splitter 36 mirror at an angle of about 45° with respect to the axis perpendicular to the surface of the lid to be subjected to examination, in correspondence of said diffuser 31 hole 32. Said beam splitter 36 mirror permits passage of radiation beam emitted from said second LED group 35" through said camera 40 visualization hole 32. Camera 40 can, thanks to said beam splitter 36, detect all radiations diffused/reflected by said lid. Said third LED group 35 diffusion lightens said lid with an α angle bigger than group of incidence angles of said second LEG group 34, substantially at about 90°, with a radiation beam substantially directed perpendicular on said lid. Therefore, said radiation beam is reflected and camera 40 detects possible defect as in image acquired as dark spot on clear background. LEDs of said third group 35 with a radiation beam at maximum frequency $f_3$ of the three frequencies provided, i.e. the blue one, and can detect both scratches on plane surfaced of the lid, and curl defects.

As it can be observed, arrangement of LED groups 33, 34 and 35 is such that at an increase of the incidence angle α corresponds to an increase of frequency of emitted radiation. Thus, it passes from a minimum incidence frequency, with detection of defect as clear spot on dark background (minimum incidence angle, minimum frequency of chosen emission range) at a maximum frequency incidence with detection of defect as dark spot on clear background (maximum incidence angle, maxima frequency of chosen emission range), thus avoiding interference between different radiation beam emitted, which otherwise occur in case of emission of frequencies from all directions (all incidence angles) and permitting lighting, and thus detection by camera 40, at the same time by all LED groups 33, 34 and 35, thus obtaining an efficient and quick detection.

It must be taken into consideration that defect detection by said processing and control unit, electronically filtering images according to the three lighting frequencies, permits easily detecting defects by said processor.

Apparatus 1 can also operate placing maximum frequency (blue) radiation beam emission LEDs with a minimum incidence angle α, i.e. grazing, and minimum frequency (red) radiation beam emission LEDs with a maximum incidence angle α, i.e. diffusion. However, positioning of red LEDs (minimum frequency) of said first group 33 with grazing minimum incidence angle α is the preferred one, since said red LEDs are more luminous and thus require a lower power in order to obtain a sufficient luminosity of diffusions of radiations on a possible defect. Therefore, said positioning is the preferred one since it permits obtaining an energetic optimization.

It must be observed that said diffuser 31 is useful to diffuse light emitted by said LEDs in order to prevent single spot lighting of each LED.

Figure 3:
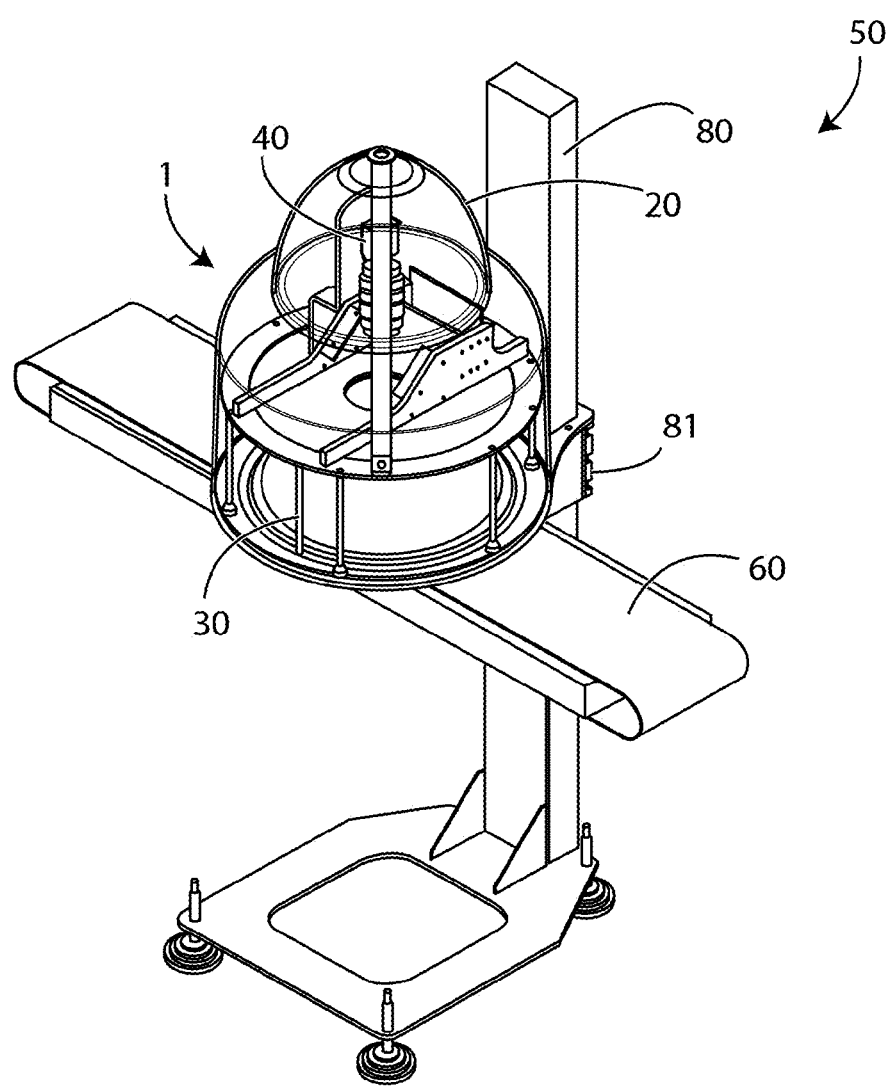
FIG. 3 shows a detection system provided with detection apparatus according to FIG. 1.
Figure 4:
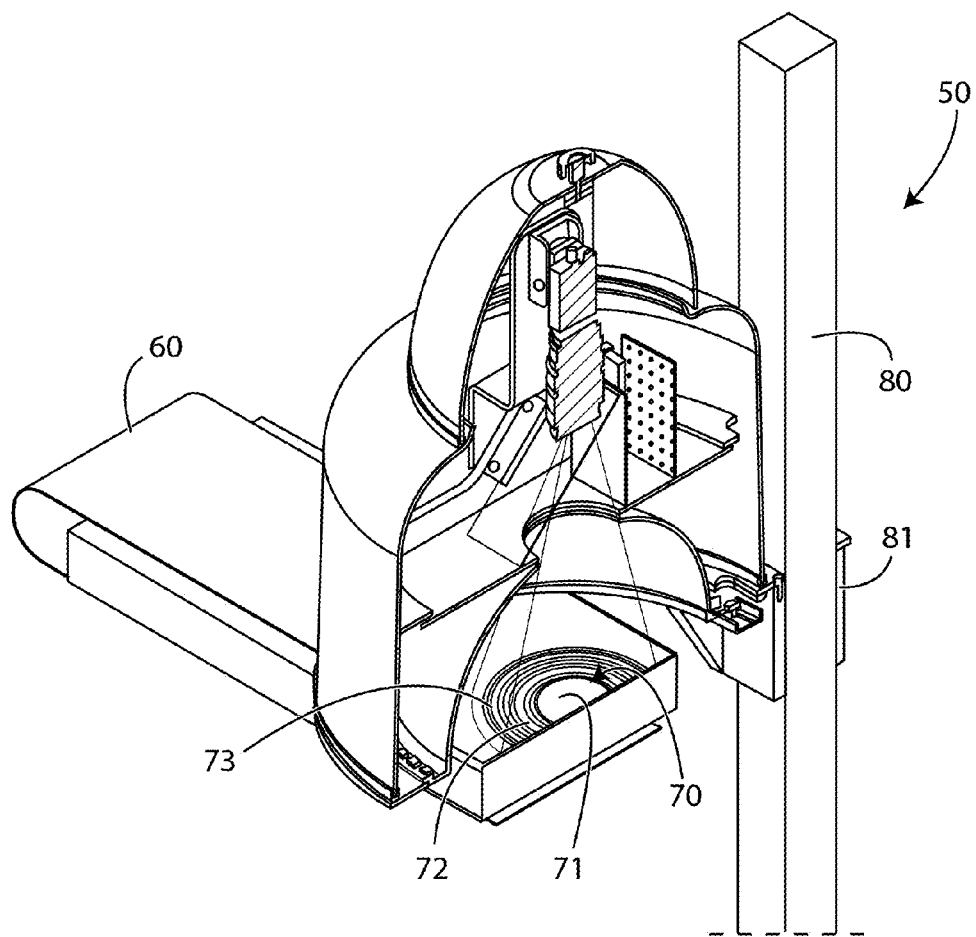
FIG. 4 shows a perspective view of a cross-section of a system according to FIG. 3.

Making now reference to FIGS. 3 and 4, it is observed a system 50 comprising a conveyor belt 60, on which lids 70 to be subjected to examination are provided, and an upright 80, on which a slide 81 is slidably coupled, on which said detection apparatus 1 is fixed. Said system 50 is provided with means, e.g. mechanical or hydraulic means, to vertically move said slide 81 along said upright 80, so as to make said apparatus 1 taking a rest position, wherein said apparatus 1 is in a raised position, and an operative position, wherein said apparatus 1 is in a lowered position, above said lid 70 to be subjected to examination, so that it is lightened, and the image can be detected. In this figure, can be noted different parts of lid 70, i.e. central portion 71, circular ribs 72 and edge curl 73.

Figure 5:
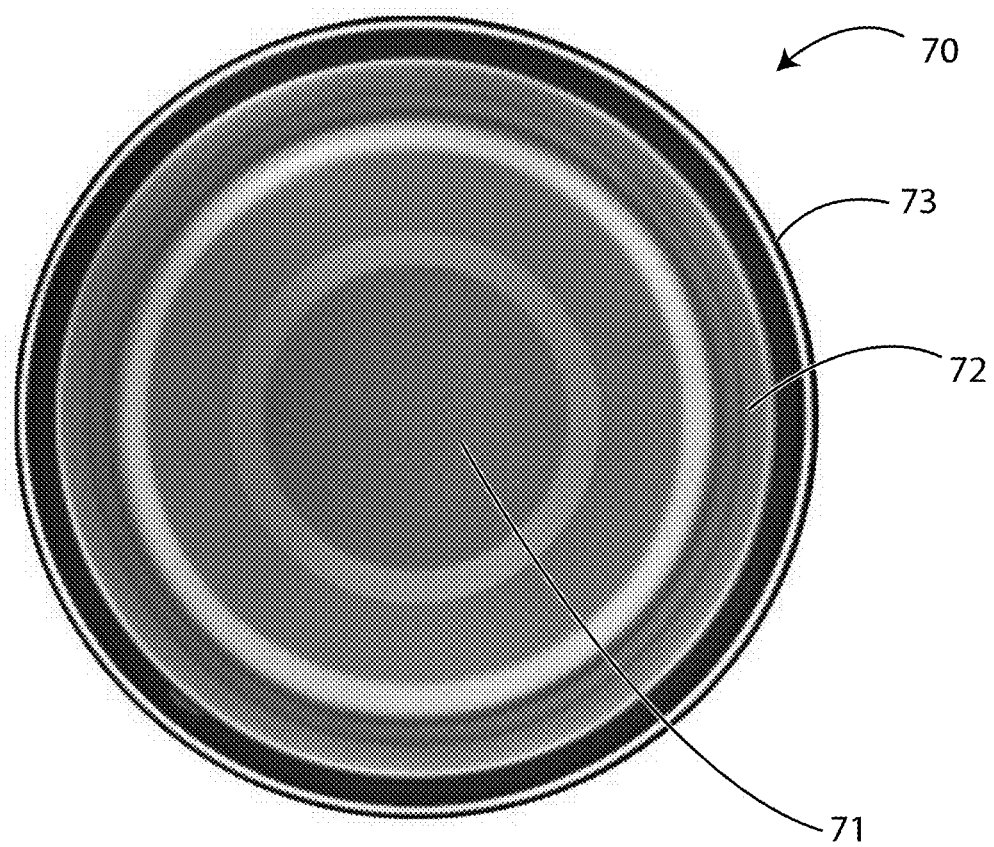
FIGS. 5-8 show defects detected on a lid by detection apparatus according to the invention.
Figure 6:
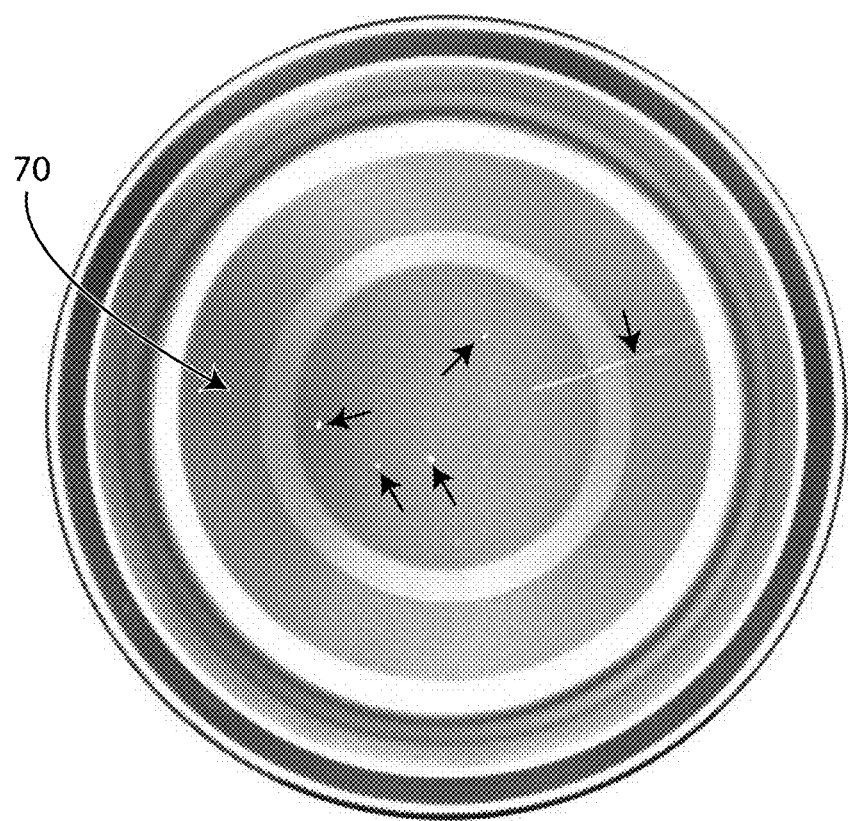
Figure 7:
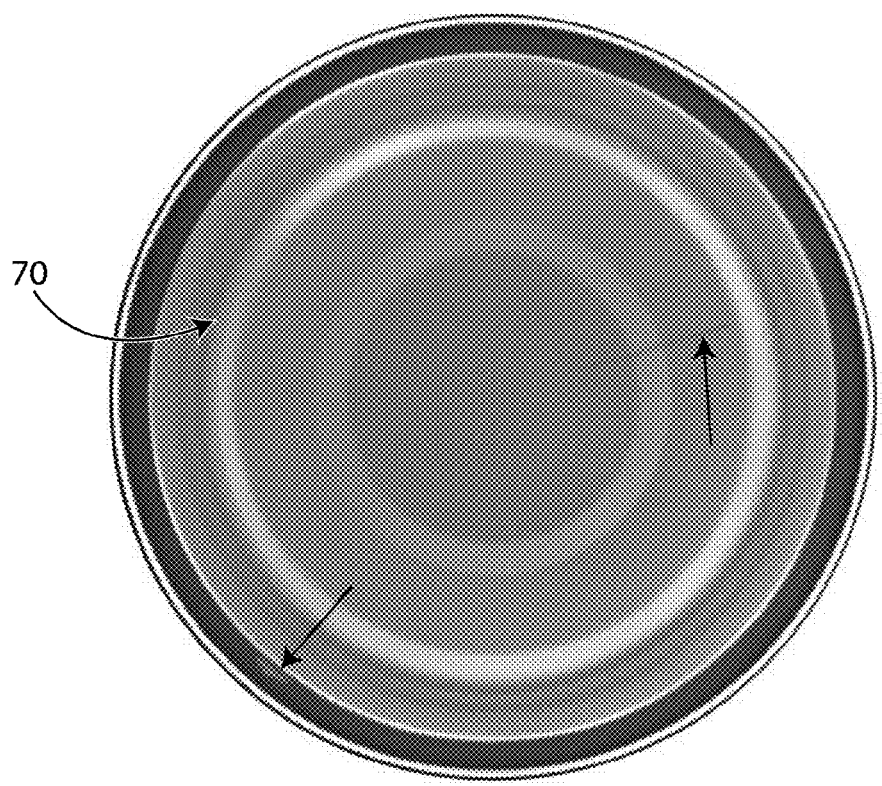
Figure 8:
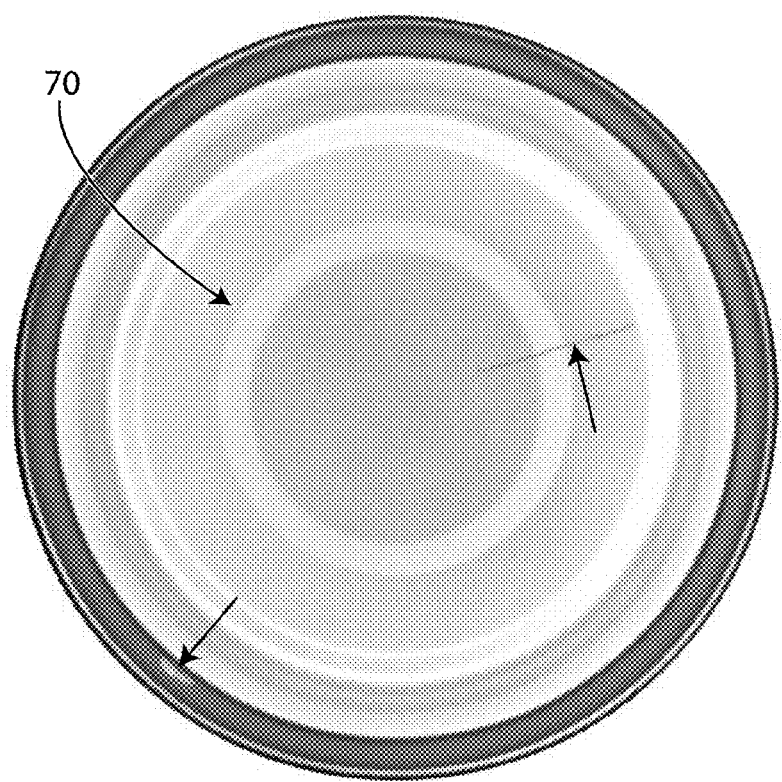

FIGS. 5-8 show images taken by camera 40, processed by said procession and control unit (not shown in the figures), that can individuate defects of lid 70 under examination. From said figures, there are observed also detected defects:

FIG. 5 show image of camera 40 of lid 70 with defects, without a processing or filtering;

FIG. 6 show lid 70, with effect of green and blue radiation beam component effect filtered, and a scratch is observed on plane central portion, passing through ribs 72 and punctiform dings always on plane central portion 71;

FIG. 7 show lid 70 of FIG. 5, with effect of red and blue radiation beam component effect filtered, and a scratch and a defect on curl 73 are observed, the latter not shown in FIG. 6; and FIG. 8 shows lid 70 of FIG. 5, with effect of red and green radiation beam component effect filtered, and a scratch and a defect are observed on curl 73, the latter not visible in FIG. 6, and better visible in FIG. 7. It must be observed that punctiform dings detected with filtering of FIG. 6 are not detected in this figure.

The above puts into evidence that different lighting at different frequencies can better show different type of defects.

Obviously, frequencies that can be used can vary also outside visible range, thus being possible also employing radiation beams at infrared and/or ultraviolet frequencies.

Present invention has been described for illustrative, but not limitative, purposes, according to its preferred embodiments, but it is to be understood that variations and/or modifications can be introduce by those skilled in the art without departing from the relevant scope as defined in the enclosed claims.

The invention claimed is:

1. An apparatus for detecting defects of an element to be subjected to examination comprising:

lighting means for lighting the element said lighting means emits radiation beams according to two or more frequencies included within a set range and comprises a plurality of LEDs for emission of said radiation beams, such that an image acquisition unit for acquisition of images is capable of detecting an image of said element lit by said lighting means, and a unit for processing images acquired by said image acquisition unit, suitable to detect said defects, wherein:

each one of said radiation beams lighting said element according to an optical path, individuates an incidence angle (α) with respect to the surface of said element, the incidence angle ($\alpha$) comprised between a grazing minimum incidence angle and a scattering maximum incidence angle, said lighting means being provided so that the incidence angle ($\alpha$) realized by the optical path of each one of said radiation beams emitted by said lighting means is directly proportional or inversely proportional to a relevant emission frequency, said lighting means comprises a diffuser having a substantially hemispherical shape, with a concavity faced downward and provided with a hole at the top of the diffuser, through which said image acquisition unit detects the image of said element said LED of said lighting means are grouped in a first, second and a third LED assembly, said first LED assembly being installed according to a ring arrangement outside of said diffuser, so as to grazingly light said element, and being suitable to emit at a first minimum frequency ($f_1$), said second LED assembly being installed according to a ring arrangement outside said diffuser, so as to light said element to be subjected to grazing scattering examination, and being suitable to emit at a second intermediate frequency ($f_2$) and said third LED assembly comprising a first LED sub-assembly, installed according to a ring arrangement above said diffuser, and a second LED sub-assembly, arranged vertically above said diffuser, so as to light said element, and being suitable to emit at a third intermediate frequency ($f_3$), and said lighting means-further comprises a beam splitter mirror, provided above said diffuser reflecting the radiation beam emitted by said second LED sub-assembly on said element to allow detection of the image of said element by said image acquisition unit.

2. The apparatus according to claim 1, wherein the grazing minimum incidence angle ($\alpha$) corresponds to the radiation beam emitted by said lighting means at the first minimum frequency ($f_1$) of said set range.

3. The apparatus according to claim 1 wherein said LEDs of said lighting means are provided such that the incidence angle ($\alpha$) of the radiation beam optical path emitted by each of the LEDs is directly proportional or indirectly proportional to the emission frequency.

4. The apparatus according to claim 1, further comprising a protection hood the protection hood being open at the bottom, within which said image acquisition unit and said lighting means are provided, the lighting means being placed under said image acquisition unit.

5. The apparatus according to claim 1, wherein said image processing unit is capable of making an image digital filtering according to each one of said two or more frequencies to automatically recognize said defects of a filtered image.

6. A system for detection of defects on elements to be subjected to examination, comprising
a conveyor belt, on which said elements are conveyed,
an upright, substantially vertical with respect to said conveyor belt,
a slide slidingly coupled with said upright, and
the apparatus according to claim 1, wherein the apparatus is fixed to said slide, such that said apparatus has a rest position raised with respect to said conveyor belt, and an operative position, in a lowered mode being above said element, so as to light said element and acquire the image.

7. The system according to claim 6, wherein the element to be subjected to examination is a metallic lid.

8. A method for detecting defects of an element to be subjected to examination, comprising:
lighting said element with the apparatus according to claim 1;
acquiring images of said element; and
processing the acquired images of said;
wherein the lighting is performed by radiation beams according to two or more frequencies included within a set range, each one of said radiation beam lighting said element according to an optical path individuating an incidence angle ($\alpha$) with respect to the surface of said element comprised between a grazing minimum incidence angle and a scattering maximum incidence angle, the incidence angle ($\alpha$) being made up of optical path of each one of said emitted radiation beams being directly or indirectly proportional to a relevant emission frequency.

9. The method according to claim 8, wherein a radiation beam emitted during the lighting of said element at a lower frequency of the two or more frequencies of said set range corresponds to said incidence angle ($\alpha$).

10. The method according to claim 8, wherein the element to be subjected to examination is a metallic lid.

11. The apparatus according to claim 1, wherein the element to be subjected to examination is a metallic lid.

12. The apparatus according to claim 1, wherein the image acquisition unit is a camera.

13. The apparatus according to claim 1, wherein the first minimum frequency is within a red field.

14. The apparatus according to claim 1, wherein the second intermediate frequency is within a green field.

15. The apparatus according to claim 1, wherein the third intermediate frequency is within a blue field.

* * * * *